(12) United States Patent
Larsen et al.

(10) Patent No.: US 7,096,877 B2
(45) Date of Patent: Aug. 29, 2006

(54) METHOD OF ESTABLISHING AT LEAST ONE ENVELOPED FLOW IN A CHANNEL

(75) Inventors: Ulrik Larsen, Holte (DK); Anders Wolff, København (DK); Pieter Telleman, Lyngby (DK)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 10/221,498

(22) PCT Filed: Mar. 9, 2001

(86) PCT No.: PCT/DK01/00156

§ 371 (c)(1),
(2), (4) Date: Nov. 26, 2002

(87) PCT Pub. No.: WO01/69203

PCT Pub. Date: Sep. 20, 2001

(65) Prior Publication Data

US 2004/0025950 A1    Feb. 12, 2004

(30) Foreign Application Priority Data

Mar. 15, 2000    (DK) ............................... 2000 00409

(51) Int. Cl.
*G05D 11/03* (2006.01)

(52) U.S. Cl. .......................... 137/9; 137/602; 137/888; 137/889

(58) Field of Classification Search .................... 137/3, 137/9, 602, 888, 889, 890, 896
See application file for complete search history.

(56) References Cited

U.S. PATENT DOCUMENTS 1,119,515 A * 12/1914 Josse et al. .................. 417/198
4,519,423 A *  5/1985 Ho et al. ..................... 137/888
4,600,302 A     7/1986 Sage, Jr.

(Continued)

FOREIGN PATENT DOCUMENTS

EP        0 158 147 A2    10/1985

(Continued)

*Primary Examiner*—Stephen M. Hepperle
(74) *Attorney, Agent, or Firm*—Scott E. Kamholz; Foley Hoag LLP

(57) ABSTRACT

With a method of establishing an enveloped flow in a channel, in the channel an envelopment area (3) with a channel section (6, 7) is configured to which a stub with an outlet is connected, where the stub, which can be configured as a polyhedron, is arranged substantially at right-angles to the envelopment area and with the plane of the outlet substantially at right-angles to the channel section. An inlet channel (9, 11) and an outlet channel (8, 10) are connected to the envelopment area. By providing a narrowing-down in the cross-section of the channel in immediate extension of the envelopment area (3), a hydrodynamic focussing of the sample fluid is achieved when a fluid, such as a sample fluid, is introduced into the stub, and a carrier fluid is introduced into the inlet channel. The advantage of the invention is that since it is necessary only to have two fluid inlets, a relatively simple structure can be established, which can be built up in a monolithic manner, e.g. by injection molding.

11 Claims, 2 Drawing Sheets

U.S. PATENT DOCUMENTS

| | | | |
|---|---|---|---|
| 4,876,458 A | | 10/1989 | Takeda et al. |
| 4,917,152 A | * | 4/1990 | Decker ........................ 137/891 |
| 4,988,619 A | | 1/1991 | Pinkel |
| 5,034,163 A | * | 7/1991 | Baltz et al. ................. 261/34.1 |
| 5,808,737 A | | 9/1998 | Edens et al. |
| 5,913,324 A | * | 6/1999 | Signer ........................... 137/3 |
| 6,159,739 A | | 12/2000 | Weigl et al. |
| 6,196,524 B1 | * | 3/2001 | Jourdan et al. ............. 261/39.2 |

FOREIGN PATENT DOCUMENTS

| | | |
|---|---|---|
| EP | 0288029 | 10/1988 |
| WO | WO 9843066 | 10/1998 |

* cited by examiner

METHOD OF ESTABLISHING AT LEAST ONE ENVELOPED FLOW IN A CHANNEL

The invention concerns a method of establishing at least one flow in a channel, where at least one carrier fluid in the channel surrounds at least one fluid flow.

Fluid flows, e.g. for use in so-called flow cytometry, are normally established by using a carrier fluid to surround a sample fluid. In this way, in connection with a hydrodynamic focussing a precise and uniform flow of the sample liquid is achieved, after which it is possible e.g. to analyse for differences in the contents of the sample fluid, or to sort particles which are in suspension in the sample fluid on the basis of a detection of e.g. their optical characteristics. The detection can be carried out, for example, by measuring the light dispersed by the particles or by measuring the fluorescence of the particles with or without dyeing with a suitable dyestuff. It is typical to use a combination of several optical characteristics.

Methods of establishing a flow have long been known. A flow, for example a coaxial flow, can thus be brought about by inserting a small tube into a larger tube. A sample fluid is fed through the smaller tube, while a carrier liquid is fed through the larger tube. In this manner, a coaxial flow is established at the mouth of the small tube, where the sample fluid is surrounded by the carrier fluid. For purely mechanical reasons, it will be obvious that this method is not suitable for mass fabrication where disposable equipment is concerned.

With the construction of flow cytometers in micro-systems, cf. e.g. WO 9843066, a flow is laminated on three sides with a carrier fluid, and it is positioned in the centre by lamination on a fourth side with a further carrier fluid. In this way, a unit in a monolithic structure can be realised by means of lithographic processes. However, an extra carrier fluid inlet is required, which makes fabrication more expensive in that the coupling of several extra tube connections is required.

Moreover, very small differences in pressure in the two carrier fluid flows will result in a displacement of the particles transversely to the direction of flow, whereby unintentional variations can arise in the measurement signals which are to be generated.

Therefore, it is an object of the invention to provide a method of establishing a flow which can be realised in a monolithic structure, where there are only two fluid inlets, namely one for carrier fluid and one for sample fluid.

A further object of the invention is to provide a method for use in the establishment of flows in structures, which allow use of mass fabrication technology, such as injection moulding.

The objects of the invention are achieved in that in the channel at least one envelopment area is formed which comprises a channel section with an outlet which extends into the envelopment area, and where the channel section lies substantially central in and substantially at right-angles to the channel, and where the plane of the outlet is substantially at right-angles to the channel section.

In this manner it is thus relatively simple to build up a monolithic structure, which is produced in injection-moulded plastic, by hot-embossing or in a thick-film structure, such as SU8, which can reduce the costs of production to a considerable degree.

The channel section can expediently be configured with a stub, which is arranged at right-angles to the channel. In this way, the flow conditions can be dimensioned for suitable conditions, in that the configuration and height of the stub have great significance for the efficiency and, among other things, are dependent on the actual Reynolds number for the relevant flow. Thus, a function interval for the flow speeds in a geometrically-fixed structure will be involved.

By configuring the stub a polyhedron, the stub which extends into the flow path can be adapted to the fluid flow, so that so-called stagnation zones and/or re-circulating flows which arise at the transition between the surface of the stub and the fluid flow are avoided, or at any rate minimised.

In an embodiment, a narrowing-down is formed in immediate extension of the envelopment area, so that an expedient construction is achieved which is suitable in planar chip-technology for combining the envelopment with hydrodynamic focussing.

By more than one channel section being formed in the envelopment area, and/or by more than one envelopment area being formed in the channel, a quick mixing of the two fluid flows can be achieved by increasing the mutual contact area, since all mixing is effected by diffusion.

Expedient embodiments of the invention are disclosed in more detail in the dependent claims.

The invention will now be explained in more detail with reference to the construction of the flow system according to the invention and shown in the drawing, in which FIG. 1 shows the construction of a channel with envelopment area according to the invention, FIG. 2 shows an embodiment for the configuration of the envelopment area, while FIGS. 3A–3E show examples of flow profiles, which can be established by means of the flow system according to the invention.

In FIG. 1, 1 indicates in its entirety a construction of a flow system for establishing a flow, which can be coaxial.

From a channel connection 9, a carrier fluid 5 is led into a channel 2 which consists of an envelopment area 3 with free ends 9 and 10 which are provided with narrowed-down areas 8,9,10,11, which function as an inlet 9,11 and an outlet channel 8,10, respectively.

As will be seen, the inlet channel consists of a cylindrical piece 9 which extends over into a conical piece 11, which is connected to the envelopment area 3.

The outlet channel similarly consists of a conical piece 8, which is connected to the envelopment area 3. This conical piece 8 is connected to a cylindrical piece 10.

In the channel 2, a channel section, here shown as a stub 6,7, which lies substantially at right-angles to the envelopment area 3, is connected to the envelopment area 3. The stub 6,7 has an outlet 14, the plane of which is at right-angles to the stub. As will also be seen, the stub 6,7 extends into the inside of the channel 2, typically into the centre of the channel.

If a fluid, such as a sample fluid containing cells or biological material, is introduced into the stub 6,7, and further via the stub 6,7 into the envelopment area 3, and carrier fluid 5 is introduced into the inlet channel 9, the fluid will be surrounded by the carrier liquid, whereby a coaxial fluid flow is established. The coaxial fluid flow becomes focussed in a hydrodynamic manner in the conical piece 8. From here, the fluid flow is led further to the outlet channel 10 and thereafter further to a not-shown part of a channel system.

FIG. 2 shows a possible construction of the narrowed-down area 3, which consists of a structure in the form of a first part 12 and a second part 13. The first and the second part, which preferably consist of monolithic parts shown separated in FIG. 2, can be joined together.

As will also be seen, in the second part a stub 7 is configured, cf. also FIG. 1.

The first and the second part can be produced by injection moulding or by micro-fabrication technology, such as is known from the semiconductor industry.

In the following, with reference to FIGS. 3A–3E of the drawing, examples are disclosed of the flow profiles, which can be established by use of the principles of the invention.

Figure 1:
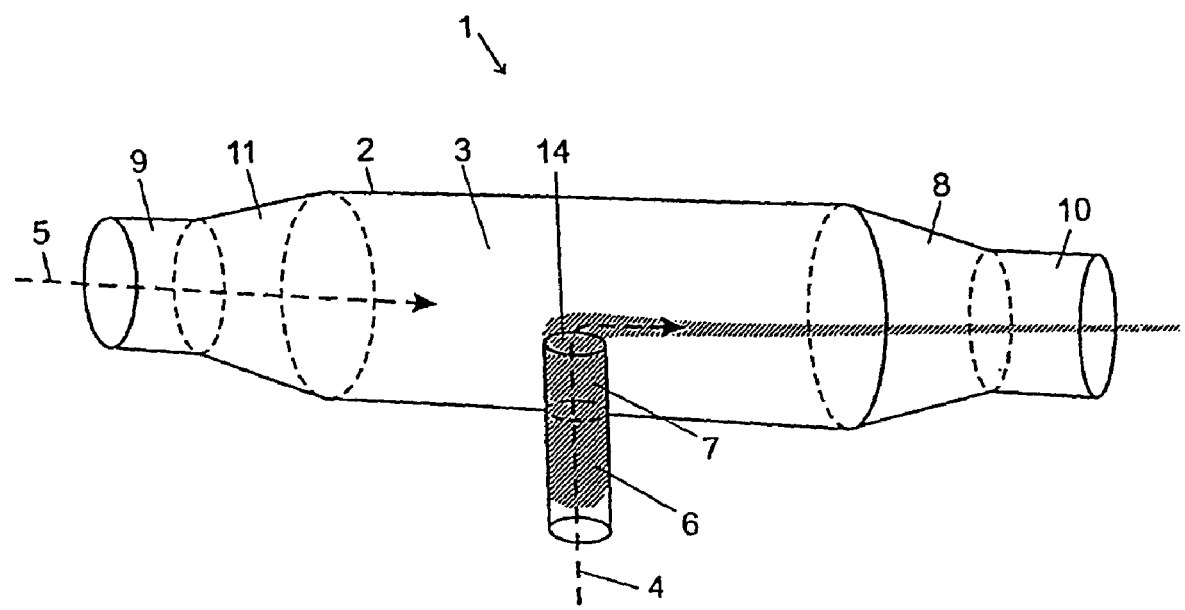
Figure 2:
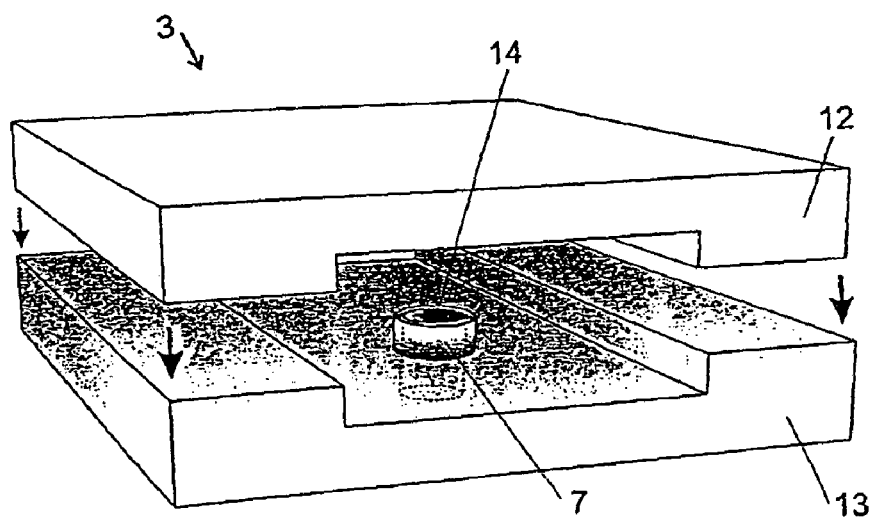
Figure 3A:
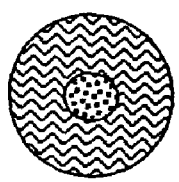
FIG. 3A shows a coaxial flow of two fluids, where e.g. a central sample fluid is surrounded by a carrier fluid.
Figure 3B:
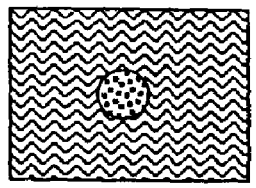
FIG. 3B shows the same type of flow profile as that in FIG. 3A, but now with a carrier fluid, which extends in a rectangular cross-section. This type can be referred to as an approximately coaxial flow.
Figure 3C:
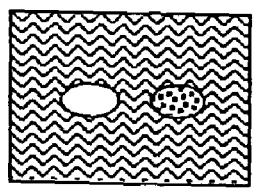
FIG. 3C shows a carrier fluid which surrounds two sample fluids.
Figure 3D:
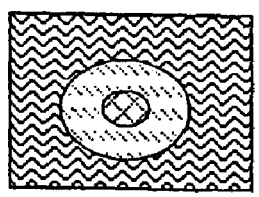
FIG. 3D shows a central, approximately coaxial flow, where a sample fluid is surrounded centrally by an inner and an outer carrier fluid.
Figure 3E:
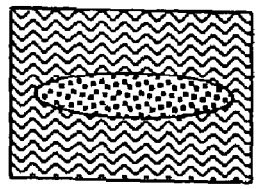

FIG. 3E corresponds to FIG. 3B, but now established with a large surface between the two fluids.

The invention claimed is:

1. A method, comprising:
    flowing a first liquid along an upstream portion of a first channel, the upstream portion of the first channel defining a first axis;
    surrounding a second liquid with the first liquid by flowing the second liquid from an exit of a second channel, the exit being located within the upstream portion of the first channel, the second channel defining a second axis oriented at a non-zero angle with respect to the first axis of the first channel; and
    hydrodynamically focusing the second liquid by flowing the first liquid and the surrounded second liquid from the upstream portion of the first channel into a downstream portion of the first channel, the upstream portion of the first channel having a minimum cross-sectional area downstream of the second channel exit, and the downstream portion of the first channel having a maximum cross-sectional area smaller than the upstream portion minimum cross-sectional area.

2. The method of claim 1, characterized in that the second channel is configured as a polyhedron.

3. The method of claim 1, characterized in that the whole of the first channel and second channel is configured in the same material.

4. The method of claim 1, characterized in that the first channel and second channel form a monolithic structure.

5. The method of claim 1, characterized in that the first channel is configured by the joining together of a first and a second part.

6. The method according to claim 1, wherein the second liquid remains surrounded by the first liquid at least to a distal end of the first channel.

7. The method of claim 1, wherein flowing the first liquid and surrounded second liquid from the upstream portion of the first channel into a downstream portion of the first channel comprises flowing the first liquid and surrounded second liquid through a tapered portion of the first channel, the tapered portion having a tapering cross-sectional area.

8. The method of claim 7, wherein the first channel further comprises a cylindrical portion downstream of the downstream portion.

9. The method of claim 1, wherein the second axis of the second channel is perpendicular to the first axis of the first channel.

10. The method of claim 1, wherein the first liquid coaxially surrounds the second liquid.

11. The method of claim 1, further comprising surrounding a third liquid with the first liquid by flowing the third liquid from an exit of a third channel, the exit being located within the upstream portion of the first channel, the third channel defining a third axis oriented at a non-zero angle with respect to the first axis of the first channel.

* * * * *